US00PP31581P3

(12) United States Plant Patent
Chang

(10) Patent No.: US PP31,581 P3
(45) Date of Patent: Mar. 24, 2020

(54) STRAWBERRY PLANT NAMED 'AMERICAN AROMA 12'

(50) Latin Name: ***Fragaria* x *ananassa* Duchesne**
Varietal Denomination: American Aroma 12

(71) Applicant: Peggy Pai-Chi Chang, Naples, FL (US)

(72) Inventor: Peggy Pai-Chi Chang, Naples, FL (US)

(73) Assignee: Peggy Pai-Chi Chang, Naples, FL (US)

( * ) Notice: Subject to any disclaimer, the term of this patent is extended or adjusted under 35 U.S.C. 154(b) by 71 days.

(21) Appl. No.: 15/998,361

(22) Filed: Aug. 8, 2018

(65) Prior Publication Data

US 2020/0053929 P1 Feb. 13, 2020

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./208, 209
CPC ..... A01H 5/0893
See application file for complete search history.

*Primary Examiner* — Kent L Bell

(57) ABSTRACT

'American Aroma 12' is a new and distinct short-day cultivar of strawberry plant, which produces large, sweet, firm and glossy fruits with early and high yield. Compared to 'Treasure' (U.S. Plant Pat. No. 12,414), 'American Aroma 12' produces larger and firmer fruit. Similar to 'Treasure', 'American Aroma 12' is also tolerant to heat, which can help Florida growers extend their growing season. 'American Aroma 12' is more resistant to strawberry anthracnose fruit rot than 'Treasure'. Because of its earliness, high yield, firmness, long shell life, excellent fruit quality, and healthiness 'American Aroma 12' is recommended for fresh market, especially for organic growers.

2 Drawing Sheets

Latin Name: *Fragaria* x *ananassa* Duchesne.
Varietal denomination: 'American Aroma 12'.

BACKGROUND OF THE INVENTION

The invention of 'American Aroma 12', a new and distinctive cultivar of strawberry plant botanically identified as *Fragaria* x *ananassa* Duch., is a result of cross breeding 'American Aroma 10' (U.S. Plant patent application Ser. No. 15/998,360) and 'AA6' (an unpatented selection). It was selected in a controlled breeding plot at a cultivated field located in Naples, Fla. during the 2012-13 fruiting season and was designated as 12067-13 by the inventor. The female parent 'American Aroma 10' is a healthy plant which is resistant to Anthracnose crown rot and has large, sweet and firm fruits with glossy red color. The male parent 'AA6' has the characteristics of earliness, high yield, and glossy fruit color with an aromatic sweet juicy fruit. 'American Aroma 12' has lighter and brighter fruit color than its female parent and larger fruit size than its male parent. 'American Aroma 12' has been asexually propagated by runner in Naples, Fla. since 2012-2013, as well as in commercial nurseries in the United States and Canada. It has been trialed in growers' fields in Florida. 'American Aroma 12' plant retains its distinctive characteristics and asexually reproduces true to type in successive generations.

SUMMARY OF THE VARIETY

'American Aroma 12', when grown in a subtropical fall and winter climate, is set apart from all other strawberry plants by a combination of high yield, early production, large firm fruit, good shape, glossy color and juicy aromatic sweet flavor.

DNA of leaf samples of 'American Aroma 12' were tested with SSR markers showing the fingerprint of 'American Aroma 12' is different from other strawberry commercial varieties from public and private sources in the database.

DESCRIPTION OF THE FIGURES

FIG. 1 depicts a) a typical mature compound leaf, b) a representative complete flower during the mid-fruiting season, c) a partial fruiting truss including different stages of flowering and fruiting, and d) a typical mature fruit.

DESCRIPTION OF THE NEW CULTIVAR

Figure 1:
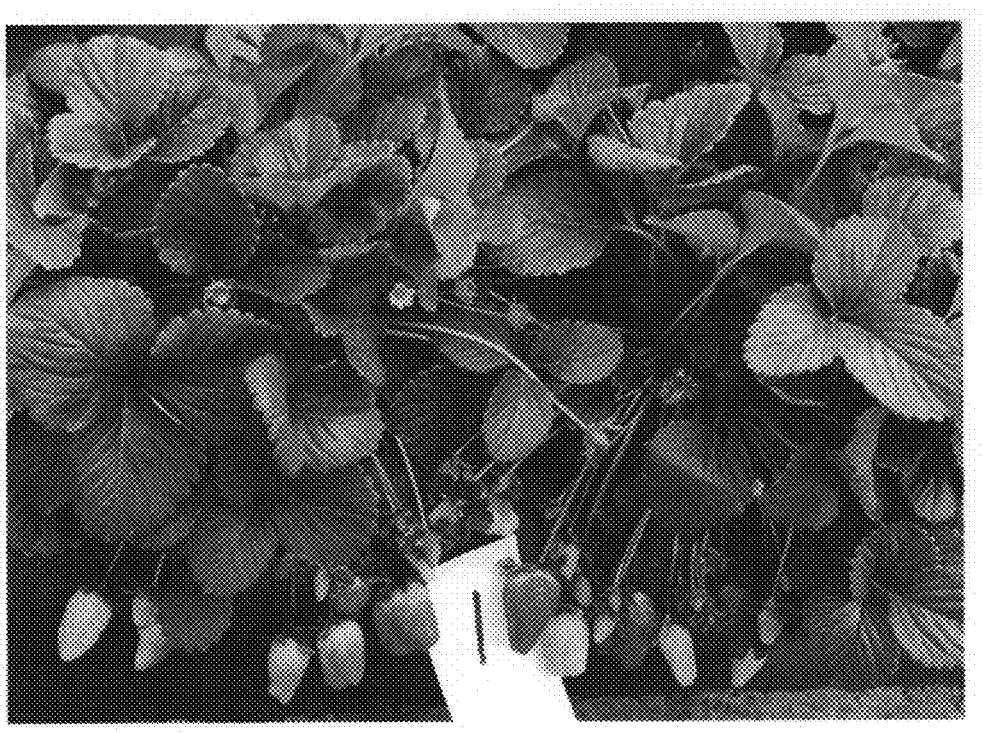
FIG. 1 shows the general growth, flowering and fruiting characteristics of the plants in late February in Florida during mid-season fruit production which is 4-5 months after planting.
Figure 2:
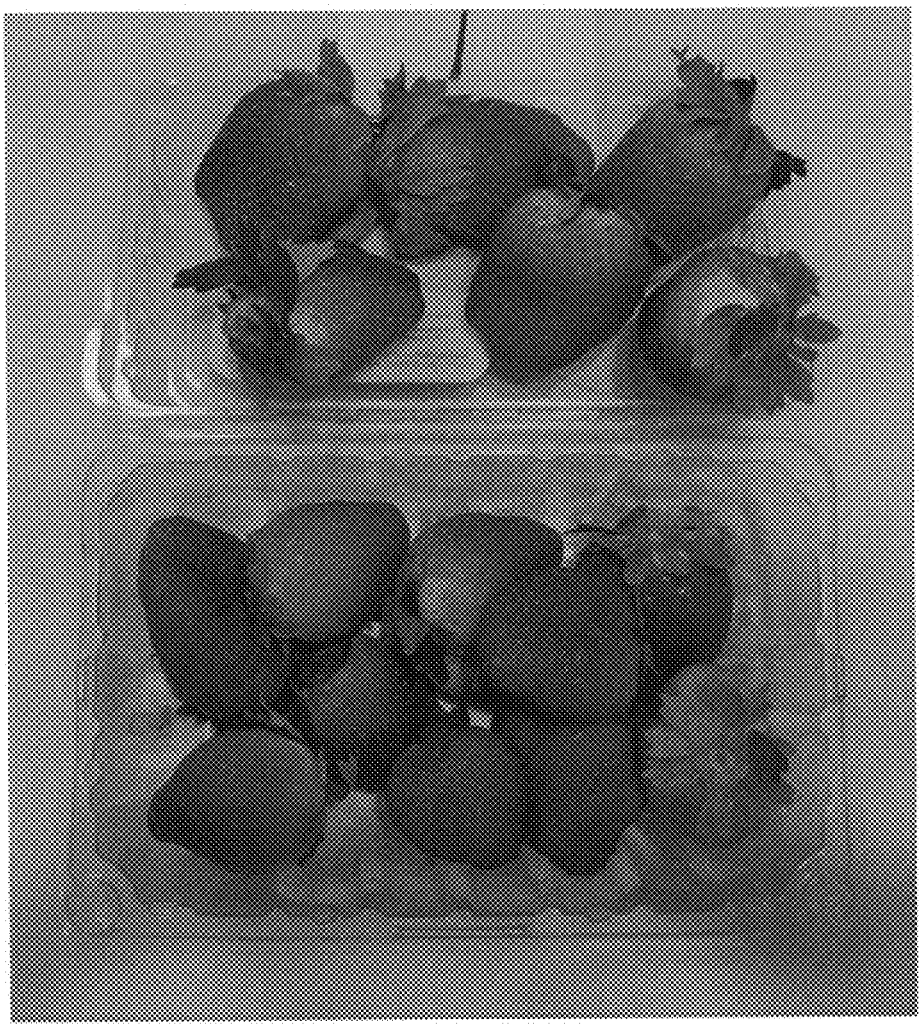
FIG. 2 shows plural fruit of one pound clam shell container reflecting the variation in fruit shape and size within market grade and shows seed and calyx placement relative to the fruit surface, as well as the attractive and uniform coloration of the ripe fruit at harvest stage.

The new cultivar 'American Aroma 12' is a healthy plant with earliness, high yield, large, sweet, firm, glossy, juicy and aromatic fruit.

The distinctive characteristics of this new strawberry cultivar, described in detail below were observed upon its discovery and throughout the repeated test periods from 2013 to 2018.

PLANTS AND FOLIAGE

The characteristics of 'American Aroma 12' described in detail below were for typical vigorous mature plants grown under warm day and cool night weather conditions, observed during February to March about 4 months after planting in Naples, Fla. The color is objectively described using Munsell Color Chart for plant tissues.

TABLE 1

Plant & Foliage Characteristics for 'American Aroma 12'

Plant:
- *Number of crowns per plant.*—4-7.
- *Average size.*—Height (mm). — 233. Diameter (mm). — 383.
- *Shape.*—Globose.
- *Density.*—Medium.
- *Vigor.*—Strong.
- *Root initiation.*—Good rooting, about 5 days to 1 week.

Foliage:
- *Number of leaflets per leaf.*—3.
- *Terminal leaflet.*—Length (mm). — 57. Width (mm). — 52.
- *Shape of terminal leaflet.*—Orbicular with serrulate margin.
- *Color (Munsell color charts).*—Apex. — Medium dark green 5GY 4/4. Base. — Medium light green 5GY 6/4 or medium green 5GY 5/4.
- *Leaf pubescence.*—Moderate and direction is acropetal.
- *Serrations number of terminal leaflets (mean).*—17.

Petiole: No plant's stipule has been found at the petiole.
- *Length (mm).*—160.
- *Diameter (mm).*—3.
- *Color (Munsell color charts).*—Light green 5GY 7/6.
- *Pubescence.*—Heavy and direction is acropetal.

Petiolule:
- *Length (mm).*—12.
- *Diameter (mm).*—2.
- *Color (Munsell color charts).*—Medium light green 5GY 6/6.
- *Base angles of terminal leaflets (half blade) (degree).*—58.

Stolons:
- *Length (mm).*—Average 430.
- *Thickness (diameter, mm).*—4
- *Number.*—Produced about 30-60 per plant, average 35.
- *Pubescence.*—Moderate and direction is acropetal.

RESISTANCE TO DISEASE

The plant of 'American Aroma 12' has been observed from 2013 to 2018 at the fruiting field in Naples, Fla. and grower trials in Plant City, Fla. during 2016-2017 and 2017-2018 seasons. It has shown healthy plants with resistance to Anthracnose crown rot and powdery mildew disease.

FLOWERING AND FRUITING CHARACTERISTICS

The distinguishing flowering and fruiting characteristics of 'American Aroma 12' plants collected in February and March at mid-season production about 4-5 months after planting are presented in Table 2. The flowers are self-fertile, and pollination is excellent. The center of the fruit is solid with little to no hollowing. It typically begins to harvest about six and a half weeks after planting in Florida commercial production areas.

TABLE 2

Flower and Fruit Characters for 'American Aroma 12'.

Bud: At the stage of largest size, 1 day before flower opens.
- *Diameter (mm).*—36.
- *Length (mm).*—20.
- *Base shape of flower bud.*—Obtuse.
- *Color (Munsell color chart).*—Upper: Medium dark green 5GY4/6. Base: Medium green 5GY 5/6.

Flower: At fully open stage, 1 day after starting to open.
- *Diameter (mm).*—40.
- *Depth (mm).*—244.
- *Number of flowers per truss.*—3 to 6.
- *Number of trusses per crown.*—3 to 5.
- *Number of crowns per plant.*—5 to 10.
- *Fragrance.*—None.
- *Bloom time and period in specific location.*—Observed at the research plots in Naples, Fla., plants were planted in mid-October and the earliest buds started opening 4 weeks after planting. Plants bloom from November until May.

Petals:
- *Length (mm).*—13.
- *Width (mm).*—9.
- *Shape.*—Obtuse. Apex: Obtuse. Base: Obtuse.
- *Color (no color chart given).*—White 5GY9/1.
- *Texture.*—Smooth.
- *Margin.*—Entire.
- *Number.*—Mean: About 7. Range: 6-7.

Sepals (calyx):
- *Length (mm).*—14.
- *Width (mm).*—9.
- *Shape.*—Oblanceolate. Apex: Acute. Base: Cuneate. Margin: Most with one point, some with three points.
- *Color (Munsell color charts).*—Abaxial: Medium dark green 5GY4/6. Adaxial: Medium light green 5GY 6/6.
- *Number.*—Mean: 11. Range: 9-14.

Reproductive organs:
- *Stamens.*—Number: 33. Length (mm): 3. Color (Munsell color charts): Yellow 5Y 8/10.
- *Pistils.*—Number & location: About 200-400 pistils attached on the surface of the receptacle. Length (mm): 1.8. Color (Munsell color charts): Yellow 5Y 8/6.
- *Fruit shape.*—Long Conic and wedge.

Fruit size & color:
- *Development stage.*—Green fruit: At maximum size about 1-2 days before starting to turn pink. Size: Length (mm): 43. Diameter (mm): 27. Color (Munsell color charts): Exterior: Medium light green 2.5GY 8/6. Flesh: Almost white 2.5GY 9/2. Pink fruit: About 1-2 days before red. Size: Length (mm): 54. Diameter (mm): 35. Color (Munsell color charts): Exterior: Glossy medium light red 7.5R 5/14. Flesh: Light red 7.5R 6/12. Ripe fruit-red:

About 1-2 days after pink. Size: Length (mm): 46-59. Diameter (mm): 35-58. Weight (gram/fruit): Average: 34. Primary: Average:39. Color (Munsell color charts): Exterior: Glossy medium red 7.5R 5/16. Flesh: Medium light red 7.5R 5/14. The fruiting truss: Length (mm): 175-210. Diameter (mm): 4-5. Number of berries per truss: 3-6.

Firmness of fruit:

*The firmness of fruit measured by fruit pressure tester equipped with* 3 *mm diameter plunger tip*.—Mean. — 839. Range. — 700-1100.

Sugar content of fruit: The sugar content or sweetness, measured as soluble solids, Mean.—9. Range—7.5-10.

Peduncle(pedicel):

*Of flowers*.—Flower at fully open stage. Length (mm): 70-98. Diameter (mm):1.5-2. Color (Munsell color charts): Light green 5GY 7/6.

*Of fruits*.—Red ripe fruit stage. Length (mm): 120-192. Diameter (mm): 2.3. Color (Munsell color charts): Medium light green 5GY 6/6.

Seeds:

*Number* (*mean*)/*fruit*.—304.

*Shape*.—Oblong.

*Size*.—Length (mm): 1-1.3. Diameter (mm): 0.5-0.8.

*Color* (*Munsell color charts*).—Light yellow 2.5Y 8/6.

*Calyx position*.—Even and center indent.

*Seed position*.—Even with skin.

The yield of 'American Aroma 12' is compared below with that of 'Treasure' & 'Florida Radiance'.

TABLE 3

Yield of strawberry cultivars at fruiting field in Naples, Florida during 2016-17 & 2017-18 seasons. Marketable yield (grams/plant)

| Cultivar | December | January | February | March | April | Total |
|---|---|---|---|---|---|---|
| 2016-17 (harvested until Apr. 11, 2017) | | | | | | |
| 'American Aroma 12' | 4.8 | 52.4 | 94.7 | 151.7 | 45.8 | 349.4 |
| 'Treasure' | 14.9 | 74.0 | 103.0 | 101.3 | 17.9 | 311.1 |
| 'Florida Radiance' | 53.1 | 52.4 | 70.8 | 83.0 | 15.8 | 275.1 |
| 2017-18 (harvested until Mar. 9, 2018) | | | | | | |
| 'American Aroma 12' | 43.1 | 75.6 | 146.0 | 62.2 | | 326.9 |
| 'Treasure' | 37.7 | 46.3 | 168.9 | 42.2 | | 295.1 |

As shown in Table 3, total yield of 'American Aroma 12' is higher than 'Treasure' and 'Florida Radiance' which is currently the dominant cultivar in the state of Florida. In 2016-17, initial plant size and plant quality of 'American Aroma 12' were not equal to those of the comparison cultivars; hence it did not produce as early as expected.

We claim:

1. A new and distinct cultivar of strawberry plant named 'American Aroma 12', as herein described and illustrated.

* * * * *